(12) United States Patent
West, Jr.

(10) Patent No.: US 9,320,510 B2
(45) Date of Patent: Apr. 26, 2016

(54) BONE ANCHORS WITH THREAD PATTERN OPTIMIZED FOR ATTACHMENT TO HARD AND SOFT BONE TISSUE

(75) Inventor: Hugh S. West, Jr., Sandy, UT (US)

(73) Assignee: HS WEST INVESTMENTS, LLC, Sandy, UT (US)

( * ) Notice: Subject to any disclaimer, the term of this patent is extended or adjusted under 35 U.S.C. 154(b) by 476 days.

(21) Appl. No.: 13/351,460

(22) Filed: Jan. 17, 2012

(65) Prior Publication Data

US 2012/0143250 A1 Jun. 7, 2012

Related U.S. Application Data

(63) Continuation of application No. 11/317,204, filed on Dec. 22, 2005, now Pat. No. 8,114,127, which is a continuation-in-part of application No. 10/873,987, filed on Jun. 22, 2004, now Pat. No. 7,322,978.

(51) Int. Cl.
*A61B 17/04* (2006.01)
*A61B 17/86* (2006.01)

(52) U.S. Cl.
CPC ........... *A61B 17/0401* (2013.01); *A61B 17/863* (2013.01); *A61B 2017/044* (2013.01); *A61B 2017/0414* (2013.01)

(58) Field of Classification Search
CPC ............. A61B 17/0401; A61B 17/863; A61B 2017/044; A61B 2017/0414; A61B 17/864
USPC ......... 606/232, 300, 301, 303, 304, 305, 308; 623/13.14
See application file for complete search history.

(56) References Cited

U.S. PATENT DOCUMENTS 3,861,269 A * 1/1975 Laverty .......................... 411/413
4,632,100 A 12/1986 Somers et al.
5,019,079 A 5/1991 Ross
(Continued)

FOREIGN PATENT DOCUMENTS

EP 0 705 572 5/1995
EP 1 584 296 4/2005
(Continued)

OTHER PUBLICATIONS

Office Action dated Apr. 17, 2007 cited in U.S. Appl. No. 10/873,987.
(Continued)

*Primary Examiner* — Tuan V Nguyen
*Assistant Examiner* — Tin Nguyen
(74) *Attorney, Agent, or Firm* — Workman Nydegger

(57) ABSTRACT

Bone anchors useful in rotator cuff repair optimize the thread pattern for engaging different types of bone tissues, including harder cortical bone and softer cancellous bone. Bone anchors may include fine threads for engaging cortical bone and coarse threads for engaging cancellous bone. Threads can be made finer by increasing root diameter and surface angle of the threads. The pitches of the fine and coarse threads are kept the same, which allows fine threads to follow the impression created by coarse threads as the anchor is driven into a bone. Threads that engage cortical bone can be multi-fluted and include a first flute that follows the same thread pattern as coarse threads such that first flute follows the groove created by the coarse threads as the bone anchor is driven into a bone. Bone anchors can have a distal non-threaded stabilizing extension at the distal end.

23 Claims, 5 Drawing Sheets

(56) References Cited

U.S. PATENT DOCUMENTS

| | | | |
|---|---|---|---|
| 5,156,616 A | 10/1992 | Meadows et al. | |
| 5,370,662 A | 12/1994 | Stone et al. | |
| 5,505,736 A | 4/1996 | Reimels et al. | |
| 5,571,139 A | 11/1996 | Jenkins, Jr. | |
| 5,573,547 A | 11/1996 | LaVeen et al. | |
| 5,573,548 A | 11/1996 | Nazre et al. | |
| 5,575,801 A | 11/1996 | Habermeyer et al. | |
| 5,584,835 A | 12/1996 | Greenfield | |
| 5,702,397 A | 12/1997 | Goble et al. | |
| 5,733,307 A | 3/1998 | Dinsdale | |
| 5,743,914 A * | 4/1998 | Skiba | 606/304 |
| 5,814,070 A | 9/1998 | Borzone et al. | |
| 5,824,011 A | 10/1998 | Stone et al. | |
| 5,851,219 A | 12/1998 | Goble et al. | |
| 5,868,789 A * | 2/1999 | Huebner | 606/232 |
| 5,891,168 A | 4/1999 | Thal | |
| 5,895,351 A | 4/1999 | Nottage et al. | |
| 5,904,704 A | 5/1999 | Goble et al. | |
| 5,935,129 A | 8/1999 | McDevitt et al. | |
| 5,957,953 A | 9/1999 | DiPoto et al. | |
| 5,961,524 A | 10/1999 | Crombie | |
| 5,964,783 A | 10/1999 | Grafton et al. | |
| 6,027,523 A | 2/2000 | Schmieding | |
| 6,045,573 A | 4/2000 | Wenstrom, Jr. et al. | |
| 6,096,060 A | 8/2000 | Fitts et al. | |
| 6,123,711 A | 9/2000 | Winters | |
| 6,139,565 A | 10/2000 | Stone et al. | |
| 6,149,653 A | 11/2000 | Deslauriers | |
| 6,159,235 A | 12/2000 | Kim | |
| 6,214,031 B1 | 4/2001 | Schmieding et al. | |
| 6,264,677 B1 | 7/2001 | Simon et al. | |
| 6,319,270 B1 | 11/2001 | Grafton et al. | |
| 6,436,124 B1 | 8/2002 | Anderson et al. | |
| 6,464,706 B1 | 10/2002 | Winter et al. | |
| 6,508,830 B2 | 1/2003 | Steiner | |
| 6,511,499 B2 | 1/2003 | Schmieding et al. | |
| 6,547,564 B1 * | 4/2003 | Hansson | 433/174 |
| 6,554,852 B1 | 4/2003 | Oberlander | |
| 6,569,186 B1 | 5/2003 | Winters et al. | |
| 6,569,188 B2 | 5/2003 | Grafton et al. | |
| 6,610,080 B2 | 8/2003 | Morgan | |
| 6,616,665 B2 | 9/2003 | Grafton et al. | |
| 6,623,492 B1 | 9/2003 | Berube et al. | |
| 6,641,596 B1 | 11/2003 | Lizardi et al. | |
| 6,648,892 B2 | 11/2003 | Martello | |
| 6,652,563 B2 | 11/2003 | Dreyfuss | |
| 6,660,023 B2 | 12/2003 | McDevitt et al. | |
| 6,666,877 B2 * | 12/2003 | Morgan et al. | 606/232 |
| 6,699,250 B1 | 3/2004 | Osterle et al. | |
| 6,743,233 B1 * | 6/2004 | Baldwin et al. | 606/323 |
| 6,840,953 B2 | 1/2005 | Martinek | |
| 6,923,824 B2 | 8/2005 | Morgan et al. | |
| 7,322,478 B2 | 1/2008 | Goto et al. | |
| 7,322,978 B2 | 1/2008 | West | |
| 7,588,587 B2 | 9/2009 | Barbieri et al. | |
| 8,114,127 B2 | 2/2012 | West | |
| 8,343,186 B2 * | 1/2013 | Dreyfuss et al. | 606/232 |
| 2001/0004694 A1 | 6/2001 | Carchidi et al. | |
| 2001/0037113 A1 | 11/2001 | Justin | |
| 2001/0053913 A1 | 12/2001 | Freedland | |
| 2002/0016594 A1 | 2/2002 | Schlapfer et al. | |
| 2002/0052629 A1 | 5/2002 | Morgan et al. | |
| 2002/0128684 A1 | 9/2002 | Foerster | |
| 2002/0147463 A1 | 10/2002 | Martinek | |
| 2002/0173822 A1 | 11/2002 | Justin et al. | |
| 2002/0183751 A1 | 12/2002 | Justin et al. | |
| 2003/0004545 A1 | 1/2003 | Burkhart et al. | |
| 2003/0065332 A1 | 4/2003 | TenHuisen et al. | |
| 2003/0065361 A1 * | 4/2003 | Dreyfuss | 606/232 |
| 2003/0074002 A1 | 4/2003 | West, Jr. | |
| 2003/0088252 A1 | 5/2003 | Kaikkonen et al. | |
| 2003/0125745 A1 | 7/2003 | Tseng et al. | |
| 2003/0144696 A1 | 7/2003 | Sinnott et al. | |
| 2003/0158555 A1 | 8/2003 | Sanders et al. | |
| 2003/0187446 A1 | 10/2003 | Overaker et al. | |
| 2003/0187477 A1 | 10/2003 | Lintner | |
| 2004/0133239 A1 | 7/2004 | Singhatat | |
| 2005/0119698 A1 | 6/2005 | Martinek | |
| 2005/0222618 A1 | 10/2005 | Dreyfuss et al. | |
| 2005/0283158 A1 | 12/2005 | West | |
| 2006/0100630 A1 | 5/2006 | West | |
| 2012/0065677 A1 | 3/2012 | West | |
| 2013/0013064 A1 | 1/2013 | West | |

FOREIGN PATENT DOCUMENTS

| | | |
|---|---|---|
| EP | 1 588 666 | 4/2005 |
| EP | 1260182 | 11/2007 |
| JP | Hei 10-507398 | 8/1998 |
| WO | WO 97/06731 | 2/1997 |
| WO | WO 00/69352 | 11/2000 |
| WO | 02/11630 | 2/2002 |
| WO | WO 2004/047617 | 6/2004 |
| WO | WO 2005/102190 | 3/2005 |

OTHER PUBLICATIONS

Notice of Allowanced dated Sep. 20, 2007 cited in U.S. Appl. No. 10/873,987.
Office Action dated Jan. 21, 2010 cited in U.S. Appl. No. 11/317,204.
Final Office Action dated May 6, 2010 cited in U.S. Appl. No. 11/317,204.
Office Action dated Dec. 8, 2010 cited in U.S. Appl. No. 11/317,204.
Final Office Action dated Apr. 6, 2011 cited in U.S. Appl. No. 11/317,204.
Office Action dated Jun. 24, 2011 cited in U.S. Appl. No. 11/317,204.
Notice of Allowanced dated Oct. 24, 2011 cited in U.S. Appl. No. 11/317,204.
U.S. Appl. No. 14/075,771, filed Nov. 8, 2013, West.
Barber, F.A., et al., Sutures and Suture Anchors: Update 2003, Arthroscopy: The Journal of Arthroscopic and Related Surgery, vol. 19, No. 9 Nov. 2003: pp. 985-990.
Barber, F.A., et al., Sutures and Suture Anchors—Update 2006, Arthroscopy: The Journal of Arthroscopic and Related Surgery, vol. 22, No. 10 Oct. 2006: pp. 1063-1069.
Office Action cited in U.S. Appl. No. 13/297,913, dated May 14, 2014.
Office Action cited in U.S. Appl. No. 13/616,623, dated Mar. 27, 2014.
Office Action cited in U.S. Appl. No. 14/075,771, dated Mar. 27, 2014.

* cited by examiner

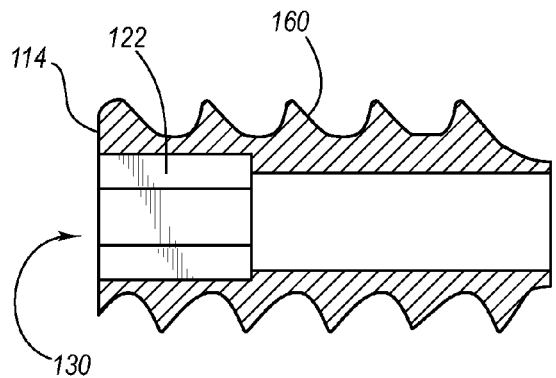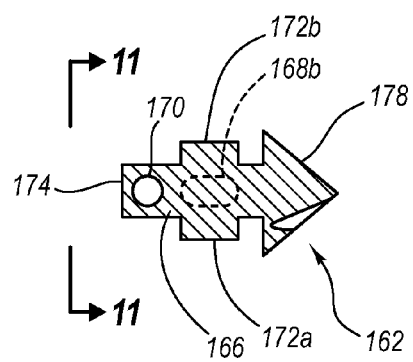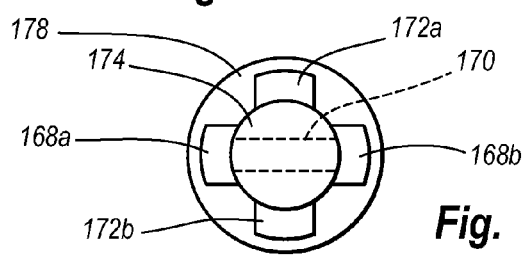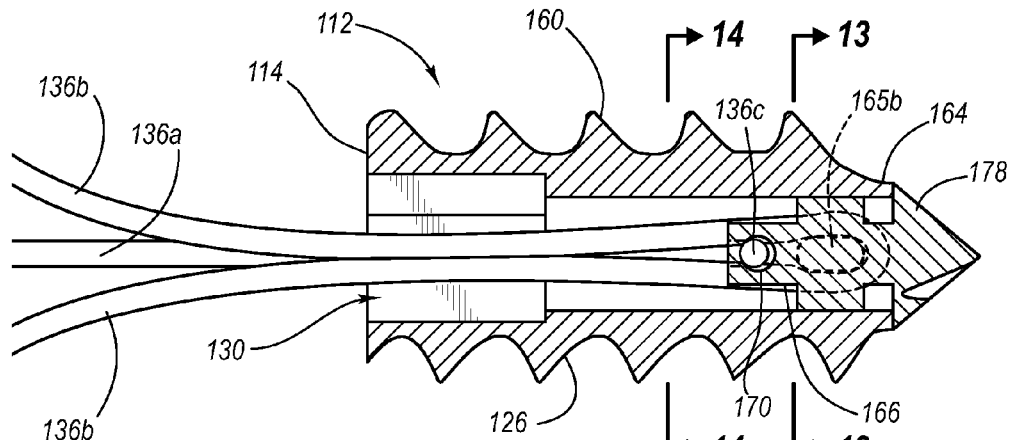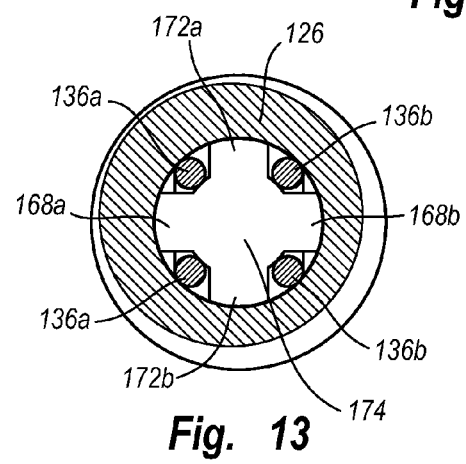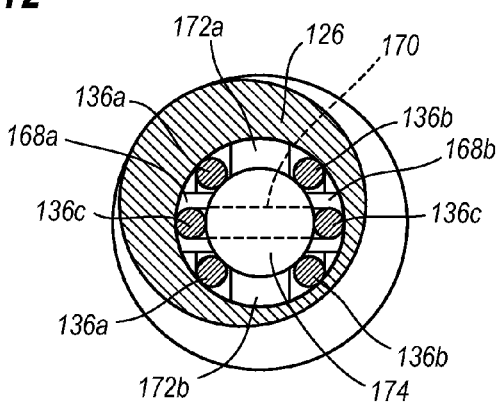

BONE ANCHORS WITH THREAD PATTERN OPTIMIZED FOR ATTACHMENT TO HARD AND SOFT BONE TISSUE

RELATED APPLICATION

This application is a continuation of U.S. patent application Ser. No. 11/317,204, filed Dec. 22, 2005, entitled "Bone Anchors For Use In Attaching Soft Tissue To Bone," now issued U.S. Pat. No. 8,114,127, which is a continuation-in-part of U.S. patent application Ser. No. 10/873,987, filed Jun. 22, 2004, now issued U.S. Pat. No. 7,322,978, the disclosures of which are incorporated herein in their entirety.

BACKGROUND OF THE INVENTION

1. The Field of the Invention

The present invention relates to soft tissue repair surgery, such as rotator cuff repair surgery. More specifically, the present invention relates to bone anchors for attaching soft tissue to bone using a suture.

2. Related Technology

Soft tissue injuries, especially rotator cuff injuries, can occur from repeated stress or acute trauma. The rotator cuff is a group of muscles and tendons in the shoulder that attach to the humerus bone of the arm. The rotator cuff allows a person to rotate the arm and raise it above the head. A common injury to the rotator cuff occurs when repeated stress or acute trauma causes the rotator cuff to partially or complete tear away from the humerus bone. These and similar types of injuries may require surgery to correctly reattach the soft tissue to the bone.

Various devices have been used to reattach soft tissue to bone. Known methods include staples, wedges, inserts, screws, and sutures alone. Threaded suture anchors, such as bone screws, have recently been developed to provide a particularly firm location where a suture can be anchored to bone. In these systems, a suture is tied between the bone anchor and soft tissue. Providing a firm attachment point for the suture is important because of the relatively strong forces that are experienced in a flexing muscle.

Despite recent advances in bone anchors, existing bone anchors and rotator cuff repairs can fail and have other disadvantages. Typically, a rotator cuff repair fails either because the bone anchor dislodges or the suture tears through the soft tissue. As force is applied to the suture, the suture can cut through the soft tissue like a cheese wire, leaving the rotator cuff detached from the humerus bone. When one suture fails, it can place more stress on the surrounding sutures, thus increasing the likelihood that other sutures will fail in like manner.

Using a greater number of sutures per unit area of soft tissue can minimize suture attachment failure. However, the number of sutures that can be used in a particular procedure is limited by the number of bone anchors that can be used and the number of sutures per anchor. During a surgical procedure, the bone anchors are placed in the humerus bone where the tissue has torn away. Thus, the number of bone anchors is limited to the number of anchors that will fit in the repair area without compromising the integrity of the humerus bone. In most rotator cuff repair surgeries, this number is two or three anchors.

The number of sutures that can be attached to each bone anchor depends on the configuration of the bone anchor. Double loading of bone anchors has been achieved for some bone anchors and is currently preferred over single loading. Typically these bone anchors have an eyelet or loop and the sutures are attached by threading the sutures through the eyelet or loop.

Loading multiple sutures on an eyelet or loop is problematic because it can cause "suture capture." During a rotator cuff repair procedure, a practitioner typically ties a knot that can be adjusted by sliding. To properly tie and adjust the knot, the suture must be able to slide in the bone anchor. Multiple sutures loaded on an eyelet or loop create friction and/or pinching that can prevent the suture from sliding in the bone anchor (i.e. causes "suture capture"). Suture capture occurs most often at the point where the sutures are sliding on the eyelet or loop of the bone anchor and after the first suture has been tied. If a first suture is tied with it crossing over an untied suture the first suture can cause friction and/or pinch the second suture against the eyelet or loop, thereby causing suture capture. As the number of sutures increases the likelihood of suture capture also increases.

Suture capture can be particularly disruptive to a surgical procedure. In many cases, if a suture becomes captured the suture can break when the practitioner attempts to adjust the knot. Because the bone anchors are small and the bone anchor is in the bone of a human when the suture breaks, it is not possible for the practitioner to thread the bone anchor with a new suture. Furthermore, it is very undesirable to remove the bone anchor once it is in place, especially if one of the sutures in the anchor has already been tied. In such cases, the bone anchor is typically left in place with only one suture. The reduced number of sutures places more strain on the soft tissue, which can increase the risk of tissue failure.

Recently, bone anchors that are less likely to cause suture capture have been developed. These anchors have two separate attachment sites inside a longitudinal bore. Attaching sutures within a longitudinal bore is particularly advantageous because it allows the bone anchor to be fully threaded (fully threaded bone anchors have threads near the proximal end that can be embedded in hard cortical bone). However, attaching sutures at different locations inside a longitudinal bore is very difficult due to size restraints. The outer diameter of a bone anchor is typically between 5.0 mm and 7.0 mm. This maximum outer diameter limits the bore diameter to between about 2.5 and 4.0 mm. Due to these size restraints, exiting bone anchors have been limited to a maximum load of two sutures.

SUMMARY

The bone anchors of the present invention overcome the disadvantages of the prior art discussed above by providing improved suture attachment sites for engaging bone tissue. In an exemplary embodiment, the bone anchors of the present invention have an anchor body extending between a proximal end and a distal end. The anchor body has a longitudinal bore that opens at the proximal end of the anchor body. At least three attachment sites are positioned within the bore. Each attachment site is capable of slidably receiving a respective suture thereon. The three attachment sites are spaced apart and configured such that the portions of the respective sutures that are in contact with the three attachment sites are maintained separated during use.

In a first embodiment, the three attachment sites are formed by placing two or more transverse pins (e.g. an upper pin and a lower pin) across the longitudinal bore. The pins are placed offset from one another such that two pins together provide three separate attachment sites. To load three sutures on the two pins, a first suture is looped on the lower pin with both ends of the suture passing by one side of the upper pin. A second suture is looped on the lower pin with both ends of the suture passing on the opposite side of the upper pin. The lower pin provides two separate attachments sites when used in combination with an upper pin because the upper pin can maintain separation between the two sutures looped on the lower pin (i.e. by passing the ends of respective sutures on opposite sides of the upper pin. A third suture attachment site is provided by the upper pin.

In a second embodiment the bone anchor comprises an anchor body having a bore that opens at a distal end of a threaded portion (in addition to the opening at the proximal end of the anchor body). A longitudinal pin is configured to be inserted into the opening at the distal end. The portion of the longitudinal pin that is inserted into the bore includes three or more suture attachment sites. In one embodiment, the inserted portion (i.e. the insert) of the longitudinal pin has two or more protrusions and one or more holes to provide three or more attachment sites for attaching sutures. The three or more attachment sites are configured to maintain the sutures separated at the point where the sutures are in contact with their respective attachment sites.

In the first and second embodiments, the attachment sites are typically formed deep within the bore to allow room for a socket to be formed in the proximal end of the anchor body. This feature allows a driver tool to be inserted for driving the bone anchor into a bone. Because the driver tool is placed on the interior of the bone anchor, the anchor body can be threaded to the proximal end. Threading the proximal end of the anchor body provides the bone anchor with the ability to better engage the cortical bone near the surface of the bone.

Providing three separate attachment sites within the bore of the bone anchors of the present invention provides several advantages not available to bone anchors with one or two sutures. Importantly, the use of three sutures can improve the success of reparatory surgery on tissue that is weak and susceptible to tearing by increasing the number of sutures per unit area. The use of a three sutures allows forces per unit area to be reduced by 67% compared to a single suture and 33% compared to a two suture anchor.

It has also been found that the use of three sutures can be beneficial even in the case where a patient's tissue is adequate to hold with only two sutures per bone anchor. The third suture can be advantageously used as a reserve in case there is a problem with one of the first two sutures, (e.g. the suture breaks, the suture is poorly placed, or a knot is loose). If the third suture is not needed, it can be easily removed. A third suture can be beneficial if a practitioner decides during an operation that the tissue needs one additional suture. If the bone anchor has a reserve suture, the practitioner can place the additional suture without adding an additional anchor. In some cases, the practitioner may want to place an odd number of sutures. Bone anchors that provide three sutures allow the practitioner to place 5 sutures, for example, using two anchors.

In another aspect of the present invention, the bone anchors can have a non-threaded portion at the distal end to form a stabilizing extension. The extension provides additional stability to the bone anchor by reducing the tendency of the anchor body to move or rotate laterally. Bone anchors are often placed in a bone at an angle. Much like a longer tent stake is less likely to give out, the extension of the bone anchor of the present invention helps prevent the bone anchor from becoming dislodged. Stabilizing the bone anchor reduces the likelihood that the bone anchor will fail and allows the bone anchor to be safely loaded with more sutures.

In yet another aspect of the invention, the anchor body is a screw that includes a portion of fine threads and a portion of coarse threads. The fine threads are configured to engage hard bone tissue, such as cortical bone, and the coarse threads are configured to engage soft bone tissue, such as cancellous bone. A portion of the threads are made finer by increasing the root diameter and increasing the surface angle of the thread. The pitch of the coarse threads and fine threads is kept the same such that the proximal threads can follow the impression created by the distal threads as the bone anchor is driven into a bone.

Optimizing the thread pattern for engaging different types of bone tissue allows the bone anchor to better engage adjacent bone tissue. Because the bone anchor can better engage adjacent bone tissue, the bone anchor can be loaded with additional sutures without compromising stability of the bone anchor. The additional sutures per anchor reduce the stress placed on each individual suture through the soft tissue, which helps prevent the sutures from cutting through the soft tissue.

These and other objects and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 10 is a cross-sectional view of the bone anchor of FIG. 8 without the sutures;

FIG. 11 is a cross-sectional view of the bone anchor of FIG. 10 along lines 11;

FIG. 12 is a cross-sectional view of the bone anchor of FIG. 9 showing the longitudinal pin inserted into the threaded portion;

FIG. 13 is a cross-sectional view of FIG. 12 along lines 13; and

FIG. 14 is a cross-sectional view of FIG. 12 along lines 14.

DETAILED DESCRIPTION OF EXEMPLARY EMBODIMENTS

Figure 1:
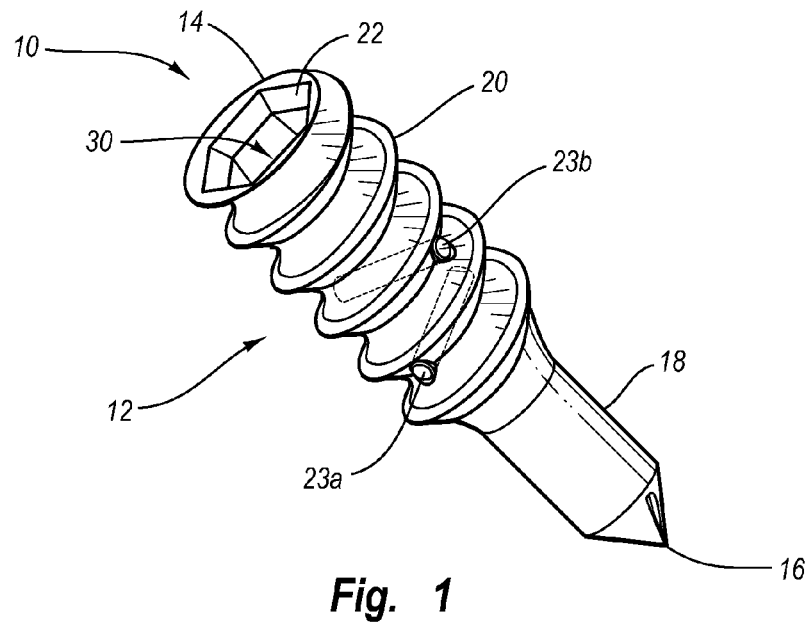
FIG. 1 is a perspective view of an exemplary bone anchor according to the invention.

With reference to FIG. 1, exemplary embodiments of the present invention are directed to an improved bone anchor 10 for affixing soft tissue to bone, such as in a rotator cuff repair surgery. Bone anchor 10 has an anchor body 12, which extends between a proximal end 14 and a distal end 16. Distal end 16 of anchor body 12 has a non-threaded portion that forms a stabilizing extension 18. Stabilizing extension 18 helps prevent lateral movement of anchor body 12 within bone tissue during use. Anchor body 12 further comprises a threaded portion, which includes threads 20 for engaging bone tissue.

Proximal end 14 includes an opening 30, which provides access to a hollow interior bore 30 of anchor body 12. A hex socket 22 is formed in bore 30 of anchor body 12, which allows bone anchor 10 to be driven into a bone using a hex driver. It will be appreciated that bore 30 of anchor body 12 can have nay other desired shape, such as triangular, square, pentagonal, star-shaped, oval, etc. Transverse pins 23a and 23b are disposed through anchor body 12 and provide attachment points for looping sutures thereon.

Figure 2:
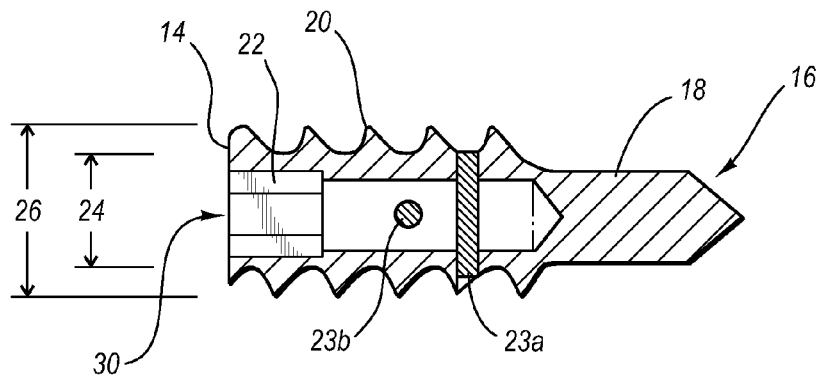
FIG. 2 is a cross-sectional view of the bone anchor of FIG. 1 showing a bore extending through the anchor body.

FIG. 2 illustrates a cross-sectional view of bone anchor 10. In an exemplary embodiment, anchor body 12 has a length of about 8 to about 15 mm, a major diameter 26 of about 5 mm, and a root diameter 24 of about 3.5 mm. Anchor body 12 can have sizes other than these; however, the size of anchor body 12 is limited by the size of the bone where the bone anchor 10 is to be placed. For example, in rotator cuff repair surgery, increasing the diameter of anchor body 12 can reduce the number of bone anchors 10 that can be positioned at the repair site.

Bone anchor 10 has threads 20 that wrap continuously around anchor body 12 in a desired (e.g., clockwise) direction. The pattern of threads 20 determines in part how bone anchor 10 engages surrounding bone tissue. In one embodiment, threads 20 make about six turns around anchor body 12 and extend toward proximal end 16.

As shown in FIG. 2, major diameter 26 and root diameter 24 may taper slightly inward toward distal end 16. The slight taper causes the threads 20 to engage bone tissue more tightly as the bone anchor 10 is driven further into a bone. Of course, bone anchor 10 can have threads that taper more or less depending on a practitioner's preference and/or the needs of a patient.

Anchor body 12 also has a non-threaded portion at distal end 16, which forms stabilizing extension 18. Stabilizing extension 18 is generally cylindrical and typically has a width less than root diameter 26. In one embodiment, the length of extension 18 is more than about 20% of the length of the threaded portion of anchor body 10. In another embodiment, extension 18 is more than 100% the length of the threaded portion and in yet another embodiment, more than about 200% of the length of the threaded portion.

In one embodiment, extension 18 is configured to be inserted into a pilot hole drilled into the bone where bone anchor 10 is to be placed. Preparing a pilot hole reduces the risk that insertion of the screw in a bone will cause damage to bone anchor 10 and/or fracture bone tissue as the bone anchor 10 is inserted into the bone. Preventing damage to bone anchor 10 and surrounding bone tissue reduces the chances that bone anchor 10 will become loosened or fail during use. In another embodiment, the bone anchor can have a self drilling distal end.

Anchor body 12 is advantageously made from a strong biocompatible material, such as a titanium alloy or stainless steel. Alternatively, anchor body 12 can be made from a biodegradable material, such as poly-l-lactic acid (PLLA) that can be absorbed into adjacent bone tissue over time as the repair site heals. Other biocompatible and/or biodegradable materials suitable for use in bone anchors are known to those skilled in the art.

Bore 30 opens at proximal end 14 to provide access to the interior of anchor body 12. In an exemplary embodiment, a proximal portion of bore 30 is hexagonally shaped to form a hex socket 22 for receiving a hex driver. This female type driver tool engagement mechanism eliminates the need to have a protruding proximal end 16. Instead, proximal end 16 is substantially flat and can be placed at or just below a bone surface, as discussed more fully below.

Figure 3:
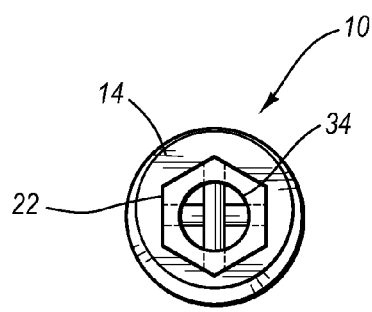
FIG. 3 is a proximal end view of the bone anchor of FIG. 1 showing a drive socket and two perpendicularly-arranged pins within the bore.

As shown in FIGS. 2 and 3, hex socket 22 can be wider than the distal portion of bore 30. For example, a ridge 34 can be formed at the distal end of hex socket 22. Ridge 34 acts as a stop to limit how deep a hex driver can be inserted therein (e.g., to protect post 23b and/or a suture attached thereto). Alternatively, the insertion depth of a hex driver can be controlled by placing a ridge of material on the hex driver. In this case, insertion of the driver would be stopped when the ridge on the driver engages the proximal end 16 of the anchor body 12.

The distal portion of bore 30 also contains one or more transverse pins for looping sutures thereon. Pins 23a and 23b are formed or inserted in anchor body 12 lying across bore 30. The diameter of pins 23a and 23b are selected such that there is sufficient space between pin 23a and pin 23b and interior surface 28 for passing a suture around the pins 23a and 23b. In addition to providing a location for looping sutures, pins 23a and 23b provide additional structural support (i.e., an endoskeleton) to anchor body 12.

Pins 23a and 23b are disposed in bore 30 substantially non-parallel to each other. As illustrated in FIG. 3, in one embodiment, pins 23a and 23b are at right angles to each other. Offsetting pins 23a and 23b exposes portions of pin 23a that would otherwise be occluded from the top by pin 23b. Such a configuration allows a suture to be loaded on pin 23a on either side of pin 24b, as shown in FIG. 4.

Figure 4:
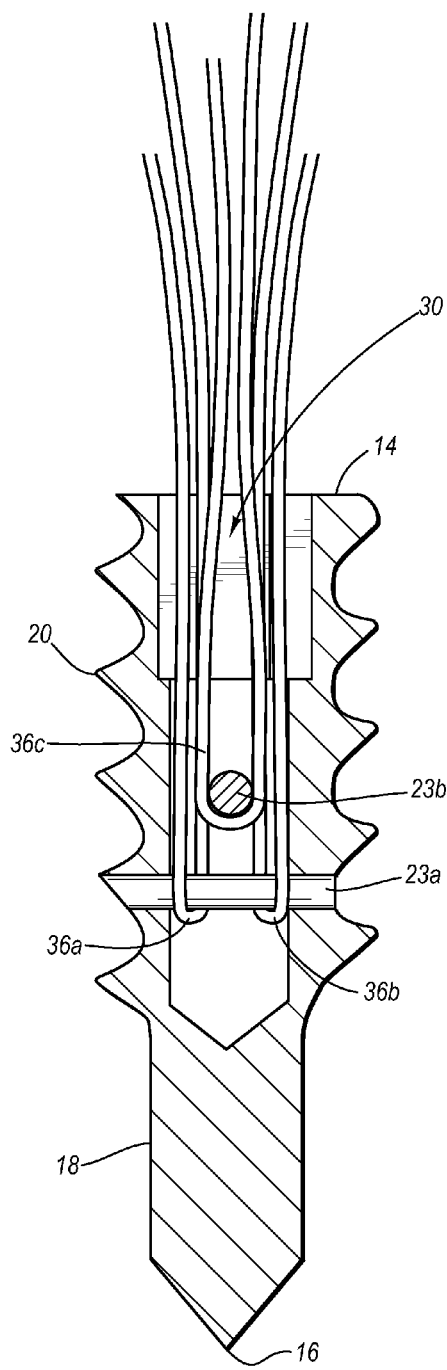
FIG. 4 is a cross-sectional view of the bone anchor of FIG. 1 with three sutures being looped around the two pins disposed in the bore.

Bone anchor 10, in FIG. 4, is illustrated loaded with three sutures 36a, 36b, and 36c (collectively sutures 36). Pin 23a is shown loaded with sutures 36a and 36b extending on either side of pin 23b. Pin 23b has a single suture 36c loaded thereon. Each suture has its own space to slide on its respective pin 23a or 23b. The proper spacing of sutures 36 in bone anchor 10 prevents sutures 36 from rubbing extensively or getting caught on one another.

Another advantageous feature of pins 23a and 23b is their position distal to hex socket 22 and within bore 30. Pins 23a and 23b are placed within bore 30 such that the forces applied by sutures 36 are transferred to a more central location within anchor body 12. Forces applied to bone anchor 10 below the surface of a bone are less likely to cause bone anchor 10 to become loosened or dislodged. Pins 23a and 23b are placed below hex socket 22 so a hex driver can be inserted without hitting the pins. This placement also allows sutures to be threaded through a hole in a driver tool (not shown) so that bone anchor 10 can be installed pre-loaded with sutures.

While bone anchor 10 has been illustrated with two pins (i.e., pins 23a and 23b), bone anchor 10 may have more or fewer pins depending on the required number of sutures and/or the space available within bore 30 for placing more sutures. For instance, in another embodiment, the anchor body 10 may have a single post with one or more sutures loaded thereon. Furthermore, a second pin can be disposed in bore 30 even where sutures are to be placed only on one pin, with the second pin being used solely to separate sutures. In addition, a second pin can be placed in anchor body 12 for structural support only.

Pins 23a and 23b are made from a strong metal or synthetic fiber so as to provide a ridged attachment point for sutures 36. In an exemplary embodiment, pins 23a and 23b are cylindrical to provide a smooth surface for sutures 36 to slide against. While pins 23a and 23b are illustrated as straight, pins 23a and 23b can be bent or have shapes other than cylindrical. Straight pins, however, can be more easily placed in anchor body 12 and therefore can reduce the cost and complexity of manufacturing bone anchor 10. The foregoing and similar attachment devices are examples of rigid attachment means for attaching a suture to an anchor.

In one embodiment, one or both of pins 23a and 23b are made from a radioopaque material such as titanium or stainless steel. A radioopaque pin can be used with a radiotransparent anchor body, such as an anchor body made from a biodegradable material such as PLLA. This configuration of materials allows a practitioner to identify and locate bone anchor 10 in a radiograph when bone anchor 10 is made mostly of biodegradable materials.

The bone anchor according to the present invention need not be formed as a threaded device, but can also be formed as a tap-in type anchor. Also, the measurements, angles and ratios between the dimensions of the bone anchor can be varied from those described above and in the following alternative embodiment so as to be suitable for the conditions and applications in which the bone anchor is to be used.

Figure 5A:
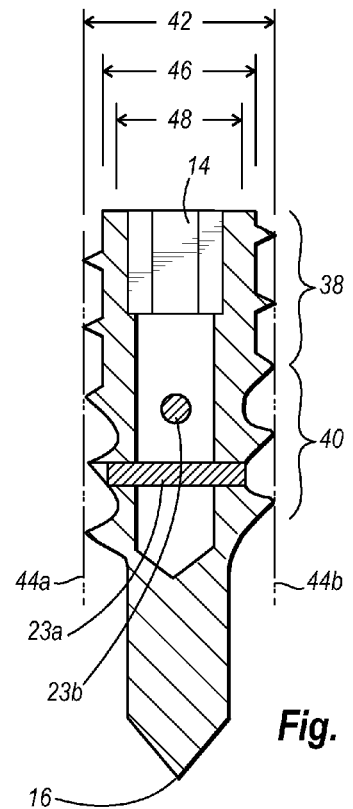
FIG. 5A illustrates an alternative embodiment of an exemplary bone anchor of the invention having finer proximal threads for engaging hard cortical bone and coarser distal threads for engaging soft cancellous bone.

FIG. 5A shows an alternative embodiment of the bone anchor of the present invention having a section of finer threads 38 (i.e., a proximal threaded section) at the proximal end 14 and a section of coarser threads 40 (i.e., a distal threaded section) distal thereto. Fine threads 38 and coarse threads 40 have the same major diameter 42 which has a slight taper illustrated by lines 44a and 44b. Fine thread 38 and coarse threads 40, have different root diameters 46 and 48 respectively. Root diameters 46 and 48 have a slight taper similar to major diameter the taper shown by lines 44a and 44b. As illustrated, the proximal threaded section constitutes less than half the length of the anchor body. Additionally, or alternatively, the proximal section can have a length that is no greater than a length of the distal threaded section.

Fine threads 38 are finer because they have a wider root diameter 46. Root diameter 46 of fine thread 38 is wider than root diameter 48 of coarse threads even after subtracting out the increase in width due to the overall taper of anchor body 12 as illustrated by lines 44a and 44b. Fine threads 38 have root diameter 46 and a major diameter 42 that are configured to engage harder bone. Coarse threads 40 have a root diameter 48 and major diameter 42 that are configured to engage soft bone. In an exemplary embodiment, major diameter 42 is about 5.3 mm. root diameter 46 is about 4.8 mm and root diameter 48 is about 3.3 mm. Fine threads 38 can have a similar shape as coarse threads 40 or a different shape as desired. For example, fine threads 38 can have a larger or smaller thread angle.

In one embodiment, fine threads 38 have the same pitch as coarse threads 40. By keeping the pitch the same between thread sections, the finer threads 38 will be able to use the same impression cut by coarse threads 40.

Figure 5B:
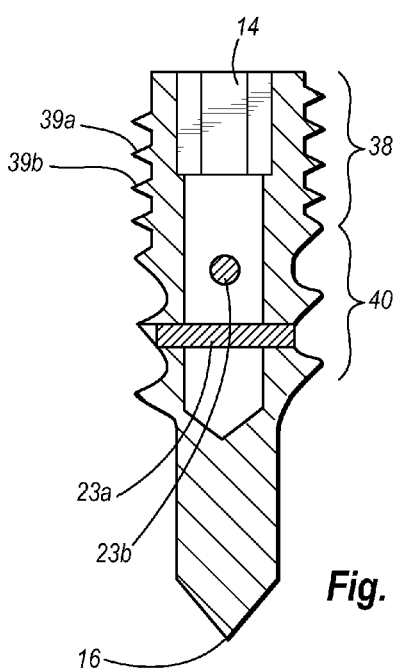
FIG. 5B illustrates the bone anchor of FIG. 5B with double flute thread on the cortical portion of the bone anchor.

FIG. 5B shows yet another alternative embodiment of the present invention where fine threads 38 form a double flute. A first flute 39a follows the thread pattern of coarse threads 40 such that first flute 39a follows the grooves created by coarse threads 40 as the bone anchor 10 is driven into a bone. In an exemplary embodiment, second flute 39b has the same pitch as first flute 39a. Second flute 39b can have a similar shape as flute 39a or a different shape as desired. For example, threads 39b can have a larger or smaller thread angle and/or major diameter.

Figure 6:
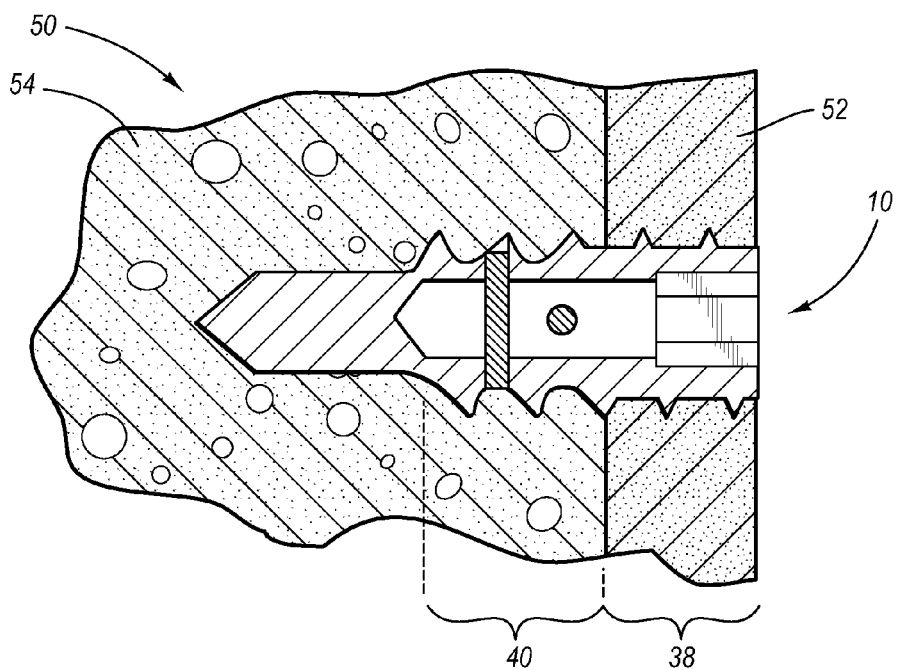
FIG. 6 illustrates the bone anchor of FIG. 5A placed within a bone such that the fine threads engage a hard cortical bone region and coarse threads engage a soft cancellous bone region.

FIG. 6 shows bone anchor 10 disposed in a typical bone 50 having a cortical bone region 52 and a cancellous bone region 54. Cortical bone region 52 comprises dense bone, while cancellous bone region 54 comprises bone that is soft or spongy. When bone anchor 10 is properly inserted into bone 50, fine threads 38 engage the hard cortical bone region 52 and coarse threads 40 engage the softer cancellous bone region 54.

In manufacturing bone anchor 10, in accordance with the present invention, anchor body 12 and posts 23 can be cast and formed in a die. Alternatively anchor body 12 can be cast or formed and posts 23a and 23b inserted later. For instance, anchor body 12 can be cast and formed from PLLA. Anchor body 12 can then be drilled to prepare holes for stainless steel pins 23a and 23b.

The suture anchors according to the present invent can be distributed to practitioners with one or more of sutures 36 threaded through bore 30 and looped to pins 23a and/or 23b. In one method of manufacturing bone anchor 10, sutures 36 are looped on pins 23a and 23b as pins 23a and 23b are inserted into anchor body 12.

An example of a type of suture suitable for use in conjunction with the bone anchor of the present invention is #2 braided polyester. If more than one strand of sutures 36 is used, the sutures can be a different color such that a practitioner can more easily pair the ends of the sutures during a surgical operation.

Figure 7:
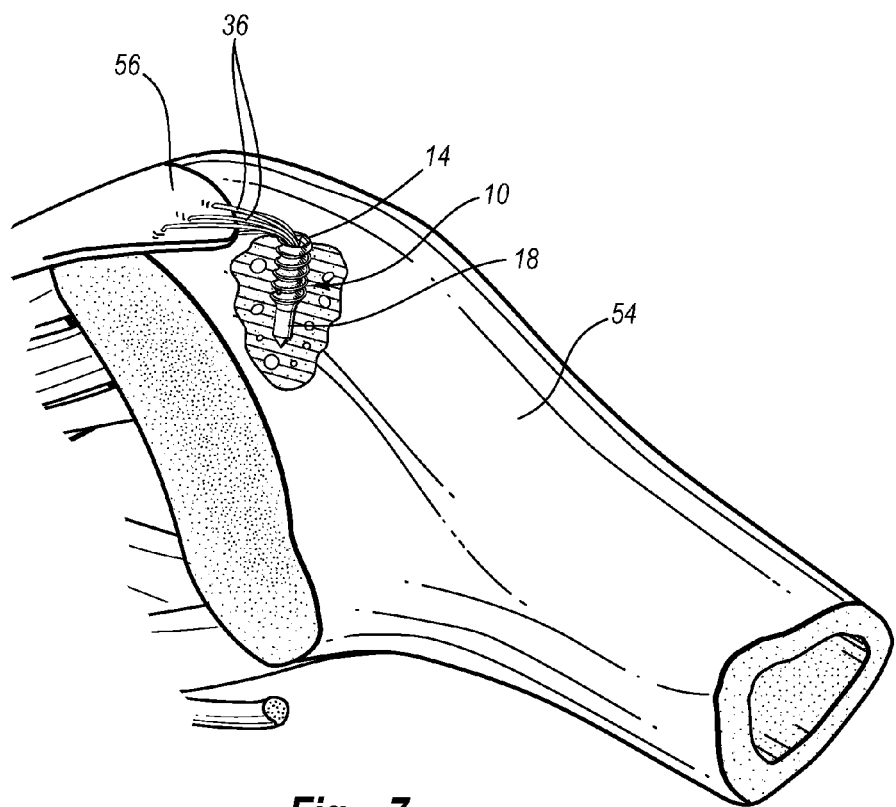
FIG. 7 illustrates an exemplary bone anchor of the invention placed in a humerus bone of a person with sutures attached to the bone anchoring being looped through and securing the person's rotator cuff.

FIG. 7 illustrates the use of bone anchor 10 in a rotator cuff repair surgery. Bone anchor 10 is placed in humerus bone 54, and sutures 36 are passed through rotator cuff 56 and tied. Before bone anchor 10 is inserted in humerus bone 54 a pilot hole may be drilled. Bone anchor 10 is inserted into the pilot hole using a driver tool until proximal end 14 is substantially flush with the outer surface of humerus bone 54. Bone anchor 10 is advantageously placed in humerus bone 54 at an angle to the tangent of the humerus bone, also known as the "dead man's angle."

Because bone anchor 10 is placed in humerus bone 54 at an angle, extension 18 provides a mechanical advantage against bone anchor 10 moving laterally and opening the angle to the tangent. By preventing lateral movement, extension 18 prevents sutures 36 from loosening once sutures 36 have been properly tied. In addition, if bone anchor 10 were to move within bone 54, bone anchor 10 can become dislodged and fail. Extension 18 does not have threads thereon, which reduce friction as bone anchor 10 is driven into a pilot hole.

Proximal end 14 of bone anchor 10 is substantially flat or non-protruding such that bone anchor 10 can be placed at or just below the surface of bone 54. Threads extend to proximal end 14 such that bone anchor 10 has maximum engagement with bone 54. The opening at proximal end 14 also allows for sutures 36 to exit the bore. The opening of the bore is smooth such that sutures 36 can easily slide thereon.

Sutures 36 exit bone anchor 10 at proximal end 14 and are drawn through the soft tissue of rotator cuff 56. Sutures 36 can be spaced to more evenly distribute the load exerted by rotator cuff 56. As shown in FIGS. 5 and 7, sutures 36 exert a force on bone anchor 10 on the pins in the bone and at proximal end 14. Because proximal end 14 is at or below the surface of bone 54, less torsion is applied to bone anchor 10. Instead, the force of rotator cuff 56 is distributed vertically along the anchor body through the pins. Consequently, bone anchor 10 is less likely to be dislodged and fail.

Figure 8:
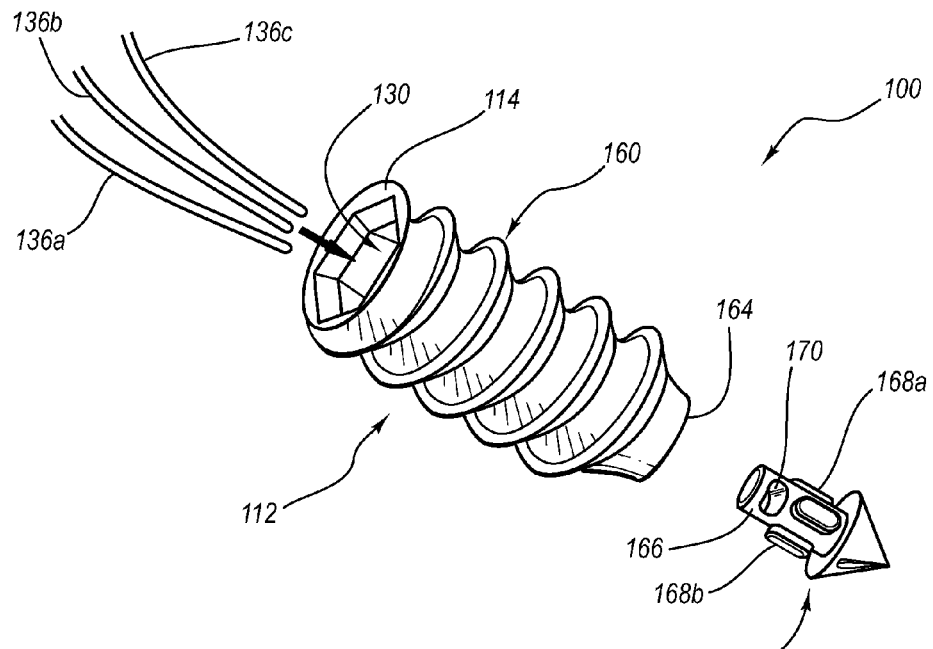
FIG. 8 is an exploded perspective view of an alternative embodiment of a bone anchor according to the present invention.

FIGS. 8-13 describe an alternative bone anchor 100 having a plurality of suture attachment sites in a longitudinal bore. As shown in FIG. 8, bone anchor 100 includes a two-piece anchor body 112 comprising a threaded portion 160 and a longitudinal pin 162. Threaded portion 160 has an interior bore 130 that opens at a proximal end 114 and at a distal end 164. Three sutures 136a, 136b, and 136c (collectively sutures 136) are shown being inserted into bore 130 of anchor body 112 via proximal end 114.

Longitudinal pin 162 includes a portion that forms an insert 166 that is configured to be received in the opening of distal end 164. Insert 166 of pin 162 includes three attachment sites for looping three respective sutures thereon. Two attachment sites are provided by protrusions 168a and 168b (collectively protrusions 168). A third attachment site is provide by a transverse hole 170.

Figure 9:
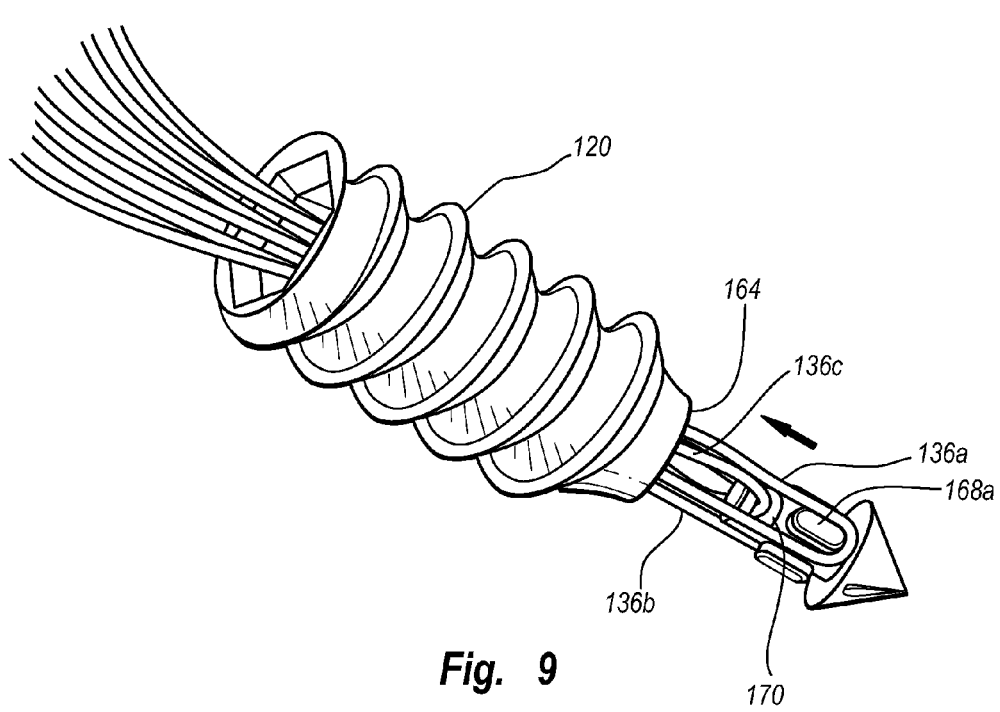
FIG. 9 illustrates the bone anchor of FIG. 8 with the three sutures looped on respective attachment sites.

FIG. 9 shows sutures 136 threaded through bore 130 and looped on the three attachment sites. Suture 136a is looped on protrusion 168a, suture 136b is looped on protrusion 168b, and suture 136c is threaded through hole 170. To secure the sutures 136, longitudinal pin 162 is inserted into bore 130 (FIG. 11).

FIG. 10 shows a cross sectional view of anchor body 112. As shown in FIG. 10, longitudinal bore 130 extends through threaded portion 160. A hex socket 122 is formed near the proximal end 114 of anchor body 112. The hex socket 122 is configured to receive a hex driver, which can be used to drive bone anchor 100 into a bone.

FIGS. 10 and 11 illustrate longitudinal pin 162. Insert 166 of pin 162 is formed from protrusions 168, spacers 172 and 172b (collectively spacers 172), and a central portion 174. Protrusions 168 and spacers 172 extend outwardly from central portion 174. Central portion 174 of insert 166 provides a physical barrier between protrusions 168a and 168b. Spacers 172 help insert 166 fit within bore 130 and act as a barrier to prevent friction between sutures during use.

FIG. 12 is a cross sectional view showing longitudinal pin 162 positioned on the distal end 164 of threaded portion 160. Insert 166 is slidably received in bore 130. Spacers 172 and protrusions 168 have an outer diameter substantially similar or slightly smaller than the diameter of bore 130 at distal end 164 such that insert portion 166 can be slidably received in bore 130. With insert 166 positioned in bore 130, protrusions 168 and spacers 172 engage wall 176 of bore 130.

While protrusions 168 have been shown having a diameter smaller than the diameter of bore 130 at distal end 164, protrusions 168 can be made wider by providing a keyway that receives the protrusions as the insert 166 is received into bore 130.

Longitudinal pin 162 is also configured to engage threaded portion 160 to prevent the insert 166 from being pulled completely through bore 130. In the embodiment shown in FIG. 11, a tip 178 engages the distal end of anchor body 160 to prevent pin 162 from sliding completely through bore 130. Those skilled in the art will recognize that other restricting mechanisms can be used to properly position insert 166 within bore 130. Tip 178 can be any shape. If desired, tip 178 can form an extension and/or can be threaded or made sharp for self-drilling.

If desired, longitudinal pin 162 can be permanently or temporarily fixed to threaded portion 160 so as to prevent pin 162 from falling out of bore 130 (i.e. movement in the longitudinal direction) and/or from rotating within bore 130. Any mechanism can be used for preventing such movement so long as it does not disrupt the spacing in bore 130 that allows sutures 136 to freely slide. In one embodiment, pin 162 can be fixed using an adhesive. Alternatively the distal end of threaded portion 160 can interlock with tip 178 to provide a mechanical restriction to rotation.

FIGS. 12-14 show an exemplary arrangement of three suture attachment sites (i.e. protrusions 168a, 168b, and transverse hole 170) within bore 130. FIG. 12, which is a cross section of anchor body 112, shows suture 136b looped around protrusion 168b. FIG. 13, which is cross-sectional view shows suture 136b in relation to 136a. As shown in FIGS. 12 and 13, suture 136b space such that it can freely slide on protrusion 168b. To allow sliding, protrusion 168b provides spacing between the central portion 178 and wall 174. Protrusion 168b extends at least to wall 174 such that suture 136b is prevented from sliding between protrusion 168b and wall 174.

Protrusion 168b is also spaced apart from tip 178 and central portion 178 provides a barrier between protrusion 168a and 168b. If desired, spacers 172 can be placed between protrusions 168a and 168b to prevent sutures 136a and 136b from coming into contact.

The spacing and arrangement of central portion 178, protrusions 168, wall 174 and tip 176 allow sutures 136a and 136b to freely slide in bore 130 and maintain the sutures separated from one another along the portion of the sutures that are in contact with protrusions 168. As can be seen in FIG. 12, sutures 136 may rub against one another within bore 130. However, this contact does not occur along the portion of sutures 136 that are in contact with the suture attachment sites (e.g. protrusions 168). Since suture capture typically occurs where a suture is in contact with the attachment site, the configuration of the present invention reduces the incidence of suture capture.

FIGS. 12 and 14 illustrate the use of hole 170 as an attachment site within bore 130. Hole 170 is made in central portion 174 of insert 166 transverse to bore 130. Sufficient space is provided between wall 176 and the exits of hole 170 to allow suture 136c to pass therebetween. In one embodiment, the exits of hole 170 are positioned over protrusions 168 (or spacers 172) so as to minimize interference between sutures 136a and/or 136b and 136c. However, since hole 170 is spaced proximally to protrusions 168, such alignment is not critical.

If desired, a second transverse hole can be made through central portion 174 to allow for placement of a fourth suture. In a preferred embodiment, this transverse hole is placed at a 90 degree angle to hole 170 such that the exits of this hole are positioned over spacers 172.

Protrusions 168 and spacers 172 can take any desired shape so long as the combination of protrusions and spacers allows sufficient space for a suture to be looped on the protrusion 168 and slide without being captured.

Bone anchor 100 can also include any of the features described above with respect to bone anchor 10. For example, bone anchor 100 can have fine and coarse threads, and extension, be made of a bioabsorbable material, and or have other similar features.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone anchor for use in attaching soft tissue to a bone having hard bone tissue and soft bone tissue, the bone anchor comprising:
an anchor body having a longitudinal axis and a length extending between a proximal end, which forms a proximal face transverse to said longitudinal axis, and a distal end, said anchor body further comprising:
an axial bore with an opening at said proximal face, at least a portion of said axial bore being shaped to form a socket for receiving a driver;
a proximal threaded section having a first flute beginning at a periphery of said proximal face and forming first threads and a second flute beginning at said periphery of said proximal face, having the same pitch as said first flute, and forming second threads between said first threads formed by said first flute; and
a distal threaded section adjacent to and extending distally from said proximal threaded section and including threads formed by a single flute having the same pitch as said first flute,
wherein said proximal threaded section has more threads per unit length than said distal threaded section and constitutes less than half the length of the anchor body,
wherein each of said proximal and distal threaded sections is positioned on said anchor body and has a length such that said proximal threaded section is configured to engage hard bone tissue and said distal threaded section is configured to engage soft bone tissue when said anchor body is fully inserted into a bone.

2. The bone anchor as in claim 1, said first threads of said proximal threaded section having the same thread pattern as said threads of said distal threaded section such that said first flute follows a groove created by said threads of said distal threaded section as the bone anchor is driven into a bone during use.

3. The bone anchor as in claim 1,
said first flute of said proximal threaded section and said single flute of said distal threaded section forming a single continuous flute extending continuously through said proximal and distal threaded sections; and
said second flute extending to said boundary between said proximal and distal threaded sections.

4. The bone anchor as in claim 1, wherein said proximal threaded section is double-fluted.

5. The bone anchor as in claim 1, said anchor body further comprising a non-threaded section extending between said distal threaded section and said distal end, wherein said non-threaded section is at least about 20% of the combined length of said proximal and distal threaded sections.

6. The bone anchor as in claim 1, further comprising at least one suture attachment site in communication with said axial bore.

7. The bone anchor as in claim 6, wherein said at least one suture attachment site accommodates attachment of at least one looped suture thereto.

8. The bone anchor as in claim 1, wherein said axial bore extends partially through said anchor body and terminates before said distal end so that said anchor body has a closed distal tip.

9. The bone anchor as in claim 1, wherein said proximal threaded section has a major diameter greater than a major diameter of said distal threaded section.

10. The bone anchor as in claim 1, wherein said proximal threaded section has a root diameter greater than a root diameter of said distal threaded section.

11. The bone anchor as in claim 1, wherein said proximal threaded section comprises fine threads and said distal threaded section comprises coarse threads.

12. The bone anchor as in claim 11, wherein said fine threads and said coarse threads have the same pitch such that one of said first or second flutes of said fine threads follows an impression created by said coarse threads as the bone anchor is driven into a bone during use.

13. The bone anchor as in claim 11, wherein said fine threads have a thread angle that is larger than a thread angle of the said coarse threads.

14. The bone anchor as in claim 1, wherein said socket is hexagonal and extends partially through said axial bore.

15. The bone anchor as in claim 1, wherein said anchor body comprises a bioabsorbable material.

16. The bone anchor as in claim 1, wherein said axial bore extends axially through said anchor body from said proximal face to beyond a boundary between said proximal and distal threaded sections.

17. A bone anchor for use in attaching soft tissue to a bone having hard bone tissue and soft bone tissue, the bone anchor comprising:
an anchor body having a longitudinal axis and a length extending between a proximal end, which forms a proximal face transverse to said longitudinal axis, and a distal end, said anchor body further comprising:
an axial bore with an opening at said proximal face, at least a portion of said axial bore being shaped to form a socket for receiving a driver;
a proximal threaded section extending circumferentially to said proximal face and having first threads formed by multiple flutes;
a distal threaded section adjacent to and extending distally from said proximal threaded section and having second threads formed by a single flute with the same pitch as at least one of said multiple flutes of said proximal threaded section; and
a non-threaded section extending between said distal threaded section and said distal end, wherein said non-threaded section is at least about 20% of the combined length of said proximal and distal threaded sections,
wherein said proximal threaded section is multi-fluted so as to have more threads per unit length than said distal threaded section and constitutes less than half the length of the anchor body,
wherein said axial bore extends axially through said anchor body from said proximal end to beyond a boundary between said proximal and distal threaded sections,
wherein each of said proximal and distal threaded sections is positioned on said anchor body and has a length such that said proximal threaded section is configured to engage hard bone tissue and said distal threaded section is configured to engage soft bone tissue when said anchor body is fully inserted into a bone.

18. The bone anchor as in claim 17, wherein said first threads of said proximal threaded section include a first flute having the same thread pattern as said second threads of said distal threaded section such that said first flute follows a groove created by said second threads as the bone anchor is driven into a bone during use.

19. The bone anchor as in claim 17, wherein said anchor body comprises:
- a first flute having a single continuous pitch and extending continuously through said proximal and distal threaded sections; and
- a second flute having the same pitch as and forming threads between threads formed by said first flute, said second flute extending through said proximal threaded section and terminating at the boundary between said proximal and distal threaded sections.

20. A bone anchor for use in attaching soft tissue to a bone having hard bone tissue and soft bone tissue, the bone anchor comprising:
- an anchor body having a longitudinal axis and extending between a proximal end, which forms a proximal face transverse to said longitudinal axis, and a distal end, said anchor body further comprising:
  - an axial bore with an opening at said proximal face, a portion of said axial bore comprising a socket having a shape configured to receive a correspondingly-shaped driver;
  - a multi-fluted proximal threaded section beginning at and extending distally from said proximal end;
  - a single-fluted distal threaded section adjacent to and extending distally from said proximal threaded section;
  - a first flute having a single continuous pitch and extending from a periphery of said proximal face, through said proximal threaded section, and into said distal threaded section; and
  - a second flute having the same pitch as said first flute and forming threads between threads formed by said first flute within said proximal threaded section,
  - wherein said axial bore extends axially through said anchor body from said proximal end to beyond said boundary between said proximal and distal threaded sections,
  - wherein each of said proximal and distal threaded sections is positioned on said anchor body and said proximal threaded section has a length that is no greater than a length of said distal threaded section such that said proximal threaded section is configured to engage hard bone tissue and said distal threaded section is configured to engage soft bone tissue when said anchor body is fully inserted into a bone.

21. The bone anchor as in claim 20, wherein said proximal threaded section is double-fluted.

22. The bone anchor as in claim 20, said first flute extending continuously through said proximal threaded section and said distal threaded section.

23. The bone anchor as in claim 20, said second flute extending continuously from said periphery of said proximal face to a boundary between said proximal and distal threaded sections.

* * * * *